United States Patent [19]

Seele et al.

[11] Patent Number: 5,102,899

[45] Date of Patent: * Apr. 7, 1992

[54] AZOLYLMETHYLOXIRANES AND FUNGICIDES CONTAINING THEM

[75] Inventors: Rainer Seele, Fussgoenheim; Walter Himmele, Walldorf; Stefan Karbach, Neustadt; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[ * ] Notice: The portion of the term of this patent subsequent to Oct. 15, 2008 has been disclaimed.

[21] Appl. No.: 493,319

[22] Filed: Mar. 14, 1990

Related U.S. Application Data

[63] Continuation of Ser. No. 310,622, Feb. 15, 1989, abandoned.

[30] Foreign Application Priority Data

Feb. 20, 1988 [DE] Fed. Rep. of Germany ....... 3805376

[51] Int. Cl.$^5$ .................... A1N 43/653; C07D 249/08
[52] U.S. Cl. .................................. 524/383; 514/184; 548/267.2; 548/267.8; 548/268.6; 548/101

[58] Field of Search ......... 548/101, 268.8, 267.2 267.8; 514/184, 383

[56] References Cited

U.S. PATENT DOCUMENTS 4,464,381  8/1984  Janssen et al. ...................... 514/382
4,612,322  9/1986  Ogata et al. .......................... 514/383

FOREIGN PATENT DOCUMENTS 061835  10/1982  European Pat. Off. ......... 548/268.6

*Primary Examiner*—Patricia L. Morris
*Attorney, Agent, or Firm*—Oblon, Spivak, McClelland, Maier & Neustadt

[57] ABSTRACT

Azolylmethyloxiranes of the general formula I

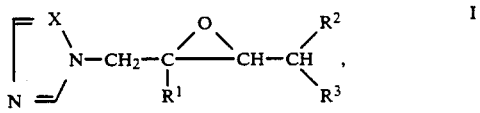

where $R^1$, $R^2$ and $R^3$ are substituted or unsubstituted alkyl, benzyl, naphthyl, biphenyl, dioxanyl, phenyl, tetrahydropyranyl, tetrahydrofuranyl, norbornyl, $C_3$–$C_{12}$-cycloalkyl or $C_3$–$C_{12}$-cycloalkenyl, and X is CH or N, and plant-tolerated acid addition salts and metal complexes thereof, and fungicides containing these compounds.

5 Claims, No Drawings

AZOLYLMETHYLOXIRANES AND FUNGICIDES CONTAINING THEM

This is a continuation of application Ser. No. 07/310,622, filed on Feb. 15, 1989, now abandoned.

The present invention relates to novel azole compounds, processes for their preparation, fungicides containing them, and methods for controlling fungi.

It is known that cis-2-(1,2,4-triazol-1-ylmethyl)-2-(tert-butyl)-3-(4-chlorophenyl)-oxirane can be used for controlling fungi (DE-3 218 130.2). However, its action is unsatisfactory.

We have found that azolymethyloxiranes of the general formula I

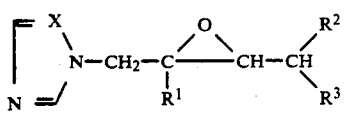

where $R^1$, $R^2$ and $R^3$ are each $C_1$-$C_{12}$-alkyl, benzyl, naphthyl, biphenyl, phenyl, dioxanyl, tetrahydropyranyl, tetrahydrofuranyl, norbornyl, $C_3$-$C_{12}$-cycloalkyl or $C_3$-$C_{12}$-cycloalkenyl, these radicals being unsubstituted or monosubstituted to trisubstituted by halogen, nitro, phenoxy, alkyl, alkoxy, amino or haloalkyl where alkyl is of 1 to 4 carbon atoms in each case, and X is CH or N, and their acid addition salts and metal complexes which are tolerated by plants have a better fungicidal action, particularly against cereal diseases, than the known azo compound.

The compounds of the formula I contain chiral centers and are generally obtained in the form of diastereomer mixtures. The diastereomers can be separated in a conventional manner, for example on the basis of their different solubilities or by column chromatography, and can be isolated in pure form. Pure enantiomers can be obtained from such an isolated diastereomer by a known method. Both the pure diastereomers or enantiomers and the mixture of these obtained in the synthesis can be used as fungicides. All these compounds are embraced by the present invention.

$R^1$, $R^2$, and $R^3$ are each, for example, methyl, ethyl, isopropyl, n-propyl, n-butyl, sec-butyl, tertbutyl, n-pentyl, neopentyl, hexyl, octyl, decyl, dodecyl, trifluoromethyl, trichloromethyl, benzyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, alkoxyphenyl, 2-methoxyphenyl, 3-methoxyphenyl, 4-methoxyphenyl, 2,4-dimethoxyphenyl, alkylphenyl, 4-ethylphenyl, 4-isopropylphenyl, 4-tert-butylphenyl, 4-tert-butoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, cyclooctyl, cyclododecyl, tetrahydropyranyl, tetrahydrofuranyl, 2-cyclohexenyl, 3-cyclohexenyl, norbornyl, 1,3-dioxan-2-yl or 1,4-dioxan-2-yl.

Acid addition salts are, for example, the hydrochlorides, bromides, sulfates, nitrates, phosphates, oxalates or dodecylbenzenesulfonates. The effectiveness of the salts is due to the cation, so that in general any anion may be chosen. The novel salts of the active ingredients are prepared by reacting the azolylmethyloxiranes with acids.

Metal complexes of the active ingredients I or of their salts can be formed with copper, zinc, tin, manganese, iron, cobalt or nickel by reacting the azolylmethyloxiranes with corresponding metal salts, for example with copper sulfate, zinc chloride, tin chloride, manganese sulfate, iron chloride, cobalt sulfate or nickel sulfate.

The compounds of the formula I can be prepared, for example, by a) reacting a compound of the formula II

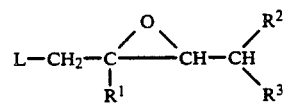

where $R^1$, $R^2$ and $R^3$ have the abovementioned meanings and L is a leaving group capable of undergoing nucleophilic substitution (OH, halogen), with a compound of the formula III

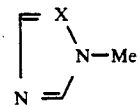

where Me is a hydrogen atom or a metal atom (Na, K) and X has the abovementioned meanings, or b) converting a compound of the formula IV

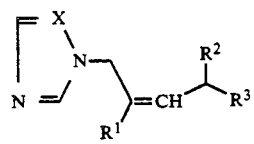

where $R^1$, $R^2$, $R^3$ and X have the abovementioned meanings, into the epoxide.

Where Me is a hydrogen atom, the reaction a) is carried out in the presence or absence of a solvent or diluent and with or without the addition of an inorganic or organic base and of a reaction accelerator at from 10° to 120° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane or corresponding mixtures.

Examples of suitable bases, which, if required, can also be used as acid acceptors in the reaction, are alkali metal hydroxides, such as lithium hydroxide, sodium hydroxide or potassium hydroxide, alkali metal carbonates, such as sodium bicarbonate, potassium bicarbonate or cesium bicarbonate, pyridine and 4-dimethylaminopyridine. However, it is also possible to use other conventional bases.

Preferred reaction accelerators are metal halides, such as sodium iodide or potassium iodide, quaternary ammonium salts, such as tetrabutylammonium chloride, bromide, iodide or hydrogen sulfate or benzyltriethylammonium chloride or bromide, and crown ethers, such as 12-crown-4, 15-crown-5, 18-crown-6, dibenzo-18-crown-6 or dicyclohexano-18-crown-6.

The reaction is carried out in general at from 20° to 150° C., under atmospheric or superatmospheric pressure, continuously or batchwise.

If Me is a metal atom, the reaction a) is carried out in the presence or absence of a solvent or diluent and with or without the addition of a strong inorganic or organic base, at from −10° to 120° C. The preferred solvents and diluents include amides, such as dimethylformamide, diethylformamide, dimethylacetamide, diethylacetamide, N-methylpyrrolidone, hexamethylphosphorotriamide, sulfoxides, such as dimethyl sulfoxide, and finally sulfolane.

Examples of suitable bases, which, if required, may also be used as acid acceptors in the reaction, are alkali metal hydrides, such as lithium hydride, sodium hydride and potassium hydride, alkali metal amides, such as sodium amide and potassium amide, and furthermore sodium tert-butoxide, potassium tert-butoxide, triphenylmethyllithium, triphenylmethylsodium, triphenylmethylpotassium, naphthalenelithium, naphthalenesodium and naphthalenepotassium.

Suitable diluents for the reaction b) are polar organic solvents, such as nitriles, e.g. acetonitrile, sulfoxides, e.g. dimethyl sulfoxide, formamides, e.g. dimethylformamide, ketones, e.g. acetone, ethers, e.g. diethyl ether or tetrahydrofuran, and, in particular, chlorohydrocarbons, e.g. methylene chloride and chloroform.

The reaction is carried out in general at from 0° to 100° C., preferably from 20° to 80° C. If a solvent is present, the reaction is advantageously carried out at the boiling point of the particular solvent.

The novel starting compounds II are obtained by epoxidation of the corresponding olefins V:

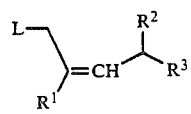

(cf. G. Dittus in Houben-Weyl-Müeller, Methoden der Organischen Chemie, Georg Thieme Verlag, Stuttgart, 1965, Vol. VI, 3, page 385).

The compound V is prepared by halogenating or oxidizing olefins of the formula VI

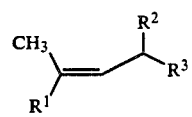

in the allyl position by a conventional method.

Suitable halogenating reagents are N-chloro- and N-bromosuccinimide in halohydrocarbons, such as carbon tetrachloride, trichloroethane or methylene chloride, at from 20° to 100° C. For allyl oxidation, peresters, such as tert-butyl perbenzoate or tert-butyl peracetate, are used in the presence of a heavy metal salt, such as copper (I) chloride or copper (I) bromide. The reaction is carried out in an inert solvent at from 10° to 100° C.

The allyl halides or allyl alcohols V thus obtained are then converted into the corresponding epoxides II (where L is halogen or OH). For this purpose, the olefins V are oxidized with a peroxycarboxylic acid, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably chlorohydrocarbon, e.g. methylene chloride, chloroform, carbon tetrachloride or dichloroethane, or, if required, in acetic acid, ethyl acetate, acetone or dimethylformamide, in the presence or absence of a buffer, such as sodium acetate, sodium carbonate or disodium hydrogen phosphate. The reaction is carried out at from 10° to 100° C. and, if necessary, is catalyzed with, for example, iodine or sodium tungstate or by means of light. Oxidation can also be carried out using alkaline solutions of hydrogen peroxide (about 30% strength) in methanol, ethanol, acetone or acetonitrile at from 25° to 30° C. or alkyl hydroperoxides, e.g. tert-butyl hydroperoxide, with the addition of a catalyst, e.g. sodium tungstate, pertungstic acid, molybdenum hexacarbonyl or vanadyl acetylacetonate. Some of the stated oxidizing agents can be produced in situ.

While the epoxyhalides thus obtained (L=halogen) can be reacted directly by process a), the corresponding epoxyalcohols II (L=OH) are converted into reactive esters, which are reacted with the compounds III by process a).

The reactive esters which are reacted with III are prepared by generally known methods (Houben-Weyl-Müller, Methoden der organischen Chemie, Georg Thieme Verlag, Stuttgart, 1955, Volume 9, pages 388, 663 and 671). Examples of such esters are methanesulfonates, trifluoromethanesulfonates, 2,2,2-trifluoroethanesulfonates, nonafluorobutanesulfonates, 4-methylbenzenesulfonates, 4-bromobenzenesulfonates, 4-nitrobenzenesulfonates and benzenesulfonates.

The compounds V can be prepared by generally known processes for olefin synthesis (Houben-Weyl-Müller, Methoden der organischen Chemie, Georg Thieme Verlag, Stuttgart, 1972, Vol. V. 1b).

The Examples which follow illustrate the preparation of the active ingredients.

I. Preparation of the Starting Compounds

Method A 4.2 g of sodium hydroxide in 30 ml of water are added to a solution of 41.5 g of 2-(4-fluorophenyl)-butanal in 200 ml of methanol. The reaction mixture is cooled to 10° C., and 36 g of 4-fluorophenylacetaldehyde are rapidly added dropwise, the temperature of the solution increasing to 30° C. Stirring is carried out for 2 hours at room temperature (20° C.), after which 200 ml of water are added to the colorless reaction solution and the resulting emulsion is extracted by shaking with methyl tert-butyl ether. The organic phase is separated off, dried over sodium sulfate and evaporated down under reduced pressure. In the subsequent distillation of the remaining residue, 34.3 g (48%) of E/Z-4-R,S-2-(4-fluorophenyl)-4-(4-fluorophenyl)-hex-2-enal are obtained under 1 mbar and at 103° C.

Method B 34.3 g of E/Z-4-R,S-2-(4-fluorophenyl)-4-(4-fluorophenyl)-hex-2-enal are dissolved in 200 ml of methanol, and 0.85 ml of concentrated sodium hydroxide solution is added. The reaction solution is stirred at 0° C. while 10.2 g of hydrogen peroxide (about 50% strength by weight) are slowly added dropwise, the internal temperature not exceeding 30° C. When the addition is complete, stirring is continued for 6 hours at room temperature, after which 1.85 g of sodium borohydride, dissolved in a little 10% strength sodium hydroxide solution, are added. After the reaction mixture has been stirred for a further 18 hours at room temperature, 100 ml of water are added to the solution, and the resulting emulsion is extracted by shaking with methylene chloride. The organic phase isolated is dried over sodium sulfate and evaporated down. 31 g (85%) of cis/trans-1'-R,S-2-hydroxymethyl-2-(4-fluorophenyl)-3-[1-(4-fluorophenyl)-prop-1-yl]-oxirane are obtained.

Method C 21 g of 4-methylbenzenesulfonyl chloride are added to a solution of 31 g of cis/trans-1'-R,S-2-hydroxymethyl-2-(4-fluorophenyl)-3-[1-(4-fluorophenyl)-prop-1-yl]-oxirane in 150 ml of methylene chloride and 20 g of triethylamine at room temperature. After 24 hours, the reaction mixture is washed with aqueous sodium bicarbonate solution and water, dried over sodium sulfate and evaporated down under reduced pressure. The residue gives 43.5 g (95%) of cis/trans-1'-R,S-2-(4-methylphenylsulfonyloxymethyl)-2-(4-fluorophenyl)-3-[1-(4-fluorophenyl)-prop-1-yl]-oxirane, which is then further processed with triazole according to the Example below.

II. Preparation of the End Products

EXAMPLE 1

8 g of sodium hydroxide are added to a solution of 14 g of 1,2,4-triazole in 150 ml of N-methylpyrrolidone, and the mixture is heated at 50° C. for 30 minutes. After the reaction mixture is cooled to room temperature, 43.5 g of cis/trans-1'-R,S-2-(4-methylphenylsulfonyloxymethyl)-2-(4-fluorophenyl)-3-[1-(4-fluorophenyl)-prop-1-yl]-oxirane, dissolved in 100 ml of N-methylpyrrolidone, are slowly added dropwise to the solution and stirring is carried out for 12 hours at room temperature. Thereafter, 200 ml of water are added and the mixture is extracted several times with methyl tert-butyl ether; the organic phase is washed with water, dried over sodium sulfate and evaporated down under reduced pressure. 36.3 g (78%) of cis/trans-1'-R,S-2-(1,2,4-triazol-1-ylmethyl)-2-(4-fluorophenyl)-3-[1-(4-fluorophenyl)-prop-1-yl]-oxirane of melting point 123°–127° C. (compound No. 1) are obtained from methyl tert-butyl ether/n-hexane.

The compounds shown in the Table can be prepared similarly to Example 1.

TABLE

| Ex. | $R^1$ | $R^2$ | $R^3$ | X | M.p./IR |
|-----|-------|-------|-------|---|---------|
| 1 | 4-F—$C_6H_4$ | $C_2H_5$ | 4-F—$C_6H_4$ | N | 123-127° C. |
| 2 | 4-F—$C_6H_4$ | $CH_3$ | 4-F—$C_6H_4$ | N | — |
| 3 | 4-F—$C_6H_4$ | $C_3H_7$ | 4-F—$C_6H_4$ | N | — |
| 4 | 4-F—$C_6H_4$ | $C_4H_9$ | 4-F—$C_6H_4$ | N | IR: 2958, 1605, 1509, 1225, 837 cm$^{-cm}$ |
| 5 | 4-F—$C_6H_4$ | tert.-butyl | 4-F—$C_6H_4$ | N | — |
| 6 | 4-F—$C_6H_4$ | benzyl | 4-F—$C_6H_4$ | N | — |
| 7 | 4-F—$C_6H_4$ | $(CH_2)_2$—phenyl | 4-F—$C_6H_4$ | N | — |
| 8 | 4-F—$C_6H_4$ | $(CH_2)_3$—phenyl | 4-F—$C_6H_4$ | N | — |
| 9 | 4-F—$C_6H_4$ | —$CH_2$—(4-F-phenyl) | 4-F—$C_6H_4$ | N | — |
| 10 | 4-F—$C_6H_4$ | —$CH_2$—(4-Cl-phenyl) | 4-F—$C_6H_4$ | N | — |
| 11 | 4-F—$C_6H_4$ | —$CH_2$—(2-Cl-phenyl) | 4-F—$C_6H_4$ | N | — |

TABLE-continued

[Structure: triazole-N-CH(R¹)-C(O epoxide)-CH(R²)(R³) with X on the triazole ring]

| Ex. | R¹ | R² | R³ | X | M.p./IR |
|---|---|---|---|---|---|
| 12 | 4-F—C₆H₄ | —CH₂—(3-Cl-C₆H₄) | 4-F—C₆H₄ | N | — |
| 13 | 4-F—C₆H₄ | —CH₂—(4-OCH₃-C₆H₄) | 4-F—C₆H₄ | N | — |
| 14 | 4-F—C₆H₄ | —CH₂—(4-tert-butyl-C₆H₄) | 4-F—C₆H₄ | N | — |
| 15 | 4-F—C₆H₄ | —CH₂—(4-NO₂-C₆H₄) | 4-F—C₆H₄ | N | — |
| 16 | 4-F—C₆H₄ | —CH₂—(4-NH₂-C₆H₄) | 4-F—C₆H₄ | N | — |
| 17 | 4-F—C₆H₄ | —(CH₂)₂—(4-Cl-C₆H₄) | 4-F—C₆H₄ | N | — |
| 18 | 4-F—C₆H₄ | —(CH₂)₂—(2-Cl-C₆H₄) | 4-F—C₆H₄ | N | — |
| 19 | 4-F—C₆H₄ | —(CH₂)₃—(4-Cl-C₆H₄) | 4-F—C₆H₄ | N | — |
| 20 | 4-F—C₆H₄ | —(CH₂)₂—(4-OCH₃-C₆H₄) | 4-F—C₆H₄ | N | — |
| 21 | 4-F—C₆H₄ | CH₃ | 2-F—C₆H₄ | N | — |
| 22 | 4-F—C₆H₄ | C₂H₅ | 2-F—C₆H₄ | N | — |
| 23 | 4-F—C₆H₄ | C₃H₇ | 2-F—C₆H₄ | N | — |
| 24 | 4-F—C₆H₄ | C₄H₉ | 2-F—C₆H₄ | N | — |
| 25 | 4-F—C₆H₄ | iso-C₃H₇ | 2-F—C₆H₄ | N | — |
| 26 | 4-F—C₆H₄ | tert.-butyl | 2-F—C₆H₄ | N | — |
| 27 | 4-F—C₆H₄ | benzyl | 2-F—C₆H₄ | N | — |
| 28 | 4-F—C₆H₄ | —CH₂—(4-F-C₆H₄) | 2-F—C₆H₄ | N | — |

TABLE-continued

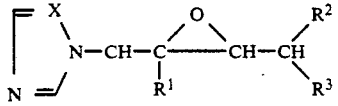

| Ex. | R¹ | R² | R³ | X | M.p./IR |
|---|---|---|---|---|---|
| 29 | 4-F—C$_6$H$_4$ | —CH$_2$—C$_6$H$_4$—Cl (4-Cl) | 2-F—C$_6$H$_4$ | N | — |
| 30 | 4-F—C$_6$H$_4$ | —CH$_2$—C$_6$H$_4$—Cl (2-Cl) | 2-F—C$_6$H$_4$ | N | — |
| 31 | 4-F—C$_6$H$_4$ | —CH$_2$—C$_6$H$_4$—NO$_2$ | 2-F—C$_6$H$_4$ | N | — |
| 32 | 4-F—C$_6$H$_4$ | —CH$_2$—C$_6$H$_4$—NH$_2$ | 2-F—C$_6$H$_4$ | N | — |
| 33 | 4-F—C$_6$H$_4$ | CH$_3$ | 2-Cl—C$_6$H$_4$ | N | — |
| 34 | 4-F—C$_6$H$_4$ | C$_2$H$_5$ | 2-Cl—C$_6$H$_4$ | N | — |
| 35 | 4-F—C$_6$H$_4$ | C$_3$H$_7$ | 2-Cl—C$_6$H$_4$ | N | — |
| 36 | 4-F—C$_6$H$_4$ | C$_4$H$_9$ | 2-Cl—C$_6$H$_4$ | N | — |
| 37 | 4-F—C$_6$H$_4$ | iso-C$_3$H$_7$ | 2-Cl—C$_6$H$_4$ | N | — |
| 38 | 4-F—C$_6$H$_4$ | tert.-butyl | 2-Cl—C$_6$H$_4$ | N | — |
| 39 | 4-F—C$_6$H$_4$ | benzyl | 2-Cl—C$_6$H$_4$ | N | — |
| 40 | 4-F—C$_6$H$_4$ | —CH$_2$—C$_6$H$_4$—F (4-F) | 2-Cl—C$_6$H$_4$ | N | — |
| 41 | 4-F—C$_6$H$_4$ | —CH$_2$—C$_6$H$_4$—Cl (4-Cl) | 2-Cl—C$_6$H$_4$ | N | — |
| 42 | 4-F—C$_6$H$_4$ | —CH$_2$—C$_6$H$_4$—Cl (2-Cl) | 2-Cl—C$_6$H$_4$ | N | — |
| 43 | 4-F—C$_6$H$_4$ | —CH$_2$—C$_6$H$_4$—NO$_2$ | 2-Cl—C$_6$H$_4$ | N | — |
| 44 | 4-F—C$_6$H$_4$ | —CH$_2$—C$_6$H$_4$—NH$_2$ | 2-Cl—C$_6$H$_4$ | N | — |
| 45 | 4-F—C$_6$H$_4$ | CH$_3$ | 3-Cl—C$_6$H$_4$ | N | m |
| 46 | 4-F—C$_6$H$_4$ | C$_2$H$_5$ | 3-Cl—C$_6$H$_4$ | N | — |
| 47 | 4-F—C$_6$H$_4$ | C$_3$H$_7$ | 3-Cl—C$_6$H$_4$ | N | — |
| 48 | 4-F—C$_6$H$_4$ | iso-C$_3$H$_7$ | 3-Cl—C$_6$H$_4$ | N | — |
| 49 | 4-F—C$_6$H$_4$ | tert.-butyl | 3-Cl—C$_6$H$_4$ | N | — |
| 50 | 4-F—C$_6$H$_4$ | benzyl | 3-Cl—C$_6$H$_4$ | N | — |

TABLE-continued $$\underset{N}{\overset{X}{\underset{\|}{N}}}-CH-\underset{R^1}{\overset{O}{\underset{|}{C}}}-CH-\underset{R^3}{\overset{R^2}{\underset{|}{CH}}}$$

| Ex. | $R^1$ | $R^2$ | $R^3$ | X | M.p./IR |
|---|---|---|---|---|---|
| 51 | 4-F—$C_6H_4$ | —$CH_2$—$C_6H_4$—F (4-F) | 3-Cl—$C_6H_4$ | N | — |
| 52 | 4-F—$C_6H_4$ | —$CH_2$—$C_6H_4$—Cl (4-Cl) | 3-Cl—$C_6H_4$ | N | — |
| 53 | 4-F—$C_6H_4$ | $CH_3$ | 4-Cl—$C_6H_4$ | N | — |
| 54 | 4-F—$C_6H_4$ | $C_2H_5$ | 4-Cl—$C_6H_4$ | N | — |
| 55 | 4-F—$C_6H_4$ | iso-$C_3H_7$ | 4-Cl—$C_6H_4$ | N | — |
| 56 | 4-F—$C_6H_4$ | tert.-butyl | 4-Cl—$C_6H_4$ | N | — |
| 57 | 4-F—$C_6H_4$ | benzyl | 4-Cl—$C_6H_4$ | N | — |
| 58 | 4-F—$C_6H_4$ | —$CH_2$—$C_6H_4$—F (4-F) | 4-Cl—$C_6H_4$ | N | — |
| 59 | 4-F—$C_6H_4$ | —$CH_2$—$C_6H_4$—Cl (4-Cl) | 4-Cl—$C_6H_4$ | N | — |
| 60 | 4-F—$C_6H_4$ | —$CH_2$—$C_6H_4$—Br (4-Br) | 4-Cl—$C_6H_4$ | N | — |
| 61 | 4-F—$C_6H_4$ | $CH_3$ | 2,4-$Cl_2$—$C_6H_3$ | N | — |
| 62 | 4-F—$C_6H_4$ | $C_2H_5$ | 2,4-$Cl_2$—$C_6H_3$ | N | — |
| 63 | 4-F—$C_6H_4$ | iso-$C_3H_7$ | 2,4-$Cl_2$—$C_6H_3$ | N | — |
| 64 | 4-F—$C_6H_4$ | tert.-butyl | 2,4-$Cl_2$—$C_6H_3$ | N | — |
| 65 | 4-F—$C_6H_4$ | benzyl | 2,4-$Cl_2$—$C_6H_3$ | N | — |
| 66 | 4-F—$C_6H_4$ | $CH_2$—$C_6H_4$—F (4-F) | 2,4-$Cl_2$—$C_6H_3$ | N | — |
| 67 | 4-F—$C_6H_4$ | $CH_2$—$C_6H_4$—Cl (4-Cl) | 2,4-$Cl_2$—$C_6H_3$ | N | — |
| 68 | 4-F—$C_6H_4$ | $C_2H_5$ | 4-Br—$C_6H_4$ | N | — |
| 69 | 4-F—$C_6H_4$ | $CH_3$ | 2-$OCH_3$—$C_6H_4$ | N | — |
| 70 | 4-F—$C_6H_4$ | $C_3H_7$ | 4-$NO_2$—$C_6H_4$ | N | — |
| 71 | 4-F—$C_6H_4$ | benzyl | 2-$CF_3$—$C_6H_4$ | N | — |
| 72 | 4-F—$C_6H_4$ | $CH_2$—$C_6H_4$—F (4-F) | 2-Cl-4-F—$C_6H_3$ | N | — |
| 73 | 4-F—$C_6H_4$ | $CH_2$—$C_6H_4$—Cl (4-Cl) | 2-Cl-6-F—$C_6H_3$ | N | — |
| 74 | 4-Cl—$C_6H_4$ | $CH_3$ | 4-F—$C_6H_4$ | N | — |
| 75 | 4-Cl—$C_6H_4$ | $C_2H_5$ | 4-F—$C_6H_4$ | N | — |
| 76 | 4-Cl—$C_6H_4$ | benzyl | 4-F—$C_6H_4$ | N | — |
| 77 | 4-Cl—$C_6H_4$ | $CH_3$ | 2-F—$C_6H_4$ | N | — |

TABLE-continued $$\begin{array}{c} \text{N} \overset{X}{=} \text{N}-\text{CH}-\overset{\text{O}}{\underset{R^1}{\text{C}}}-\text{CH}-\text{CH}\overset{R^2}{\underset{R^3}{}} \end{array}$$

| Ex. | R¹ | R² | R³ | X | M.p./IR |
|---|---|---|---|---|---|
| 78 | 4-Cl—C₆H₄ | C₂H₅ | 2-F—C₆H₄ | N | — |
| 79 | 4-Cl—C₆H₄ | benzyl | 2-F—C₆H₄ | N | — |
| 80 | 4-Cl—C₆H₄ | CH₃ | 2-Cl—C₆H₄ | N | — |
| 81 | 4-Cl—C₆H₄ | CH₂—C₆H₄—F | 2-Cl—C₆H₄ | N | — |
| 82 | 4-Cl—C₆H₄ | C₂H₅ | 3-Cl—C₆H₄ | N | — |
| 83 | 4-Cl—C₆H₄ | —CH₂—C₆H₄—Cl | 3-Cl—C₆H₄ | N | — |
| 84 | 4-Cl—C₆H₄ | C₂H₅ | 4-Cl—C₆H₄ | N | — |
| 85 | 4-Cl—C₆H₄ | CH₂—C₆H₄—F | 4-Cl—C₆H₄ | N | — |
| 86 | 4-Cl—C₆H₄ | CH₃ | 2,4-Cl₂—C₆H₃ | N | — |
| 87 | 4-Cl—C₆H₄ | benzyl | 2,4-Cl₂—C₆H₃ | N | — |
| 88 | 2-Cl—C₆H₄ | CH₃ | 4-F—C₆H₄ | N | — |
| 89 | 2-Cl—C₆H₄ | benzyl | 4-F—C₆H₄ | N | — |
| 90 | 2-Cl—C₆H₄ | CH₃ | 2-F—C₆H₄ | N | — |
| 91 | 2-Cl—C₆H₄ | —CH₂—C₆H₄—F | 2-F—C₆H₄ | N | — |
| 92 | 2-Cl—C₆H₄ | C₂H₅ | 2-Cl—C₆H₄ | N | — |
| 93 | 2-Cl—C₆H₄ | benzyl | 2-Cl—C₆H₄ | N | — |
| 94 | 2-Cl—C₆H₄ | CH₃ | 4-Cl—C₆H₄ | N | — |
| 95 | 2-Cl—C₆H₄ | —CH₂—C₆H₄—Cl | 4-Cl—C₆H₄ | N | — |
| 96 | 2-Cl—C₆H₄ | CH₃ | 2,4-Cl₂—C₆H₃ | N | — |
| 97 | 2-Cl—C₆H₄ | benzyl | 2,4-Cl₂—C₆H₃ | N | — |
| 98 | 2-Cl—C₆H₄ | CH₃ | 3-Cl—C₆H₄ | N | — |
| 99 | 2-Cl—C₆H₄ | benzyl | 3-Cl—C₆H₄ | N | — |
| 100 | 2,4-Cl₂—C₆H₃ | C₂H₅ | 4-F—C₆H₄ | N | — |
| 101 | 2,4-Cl₂—C₆H₃ | benzyl | 4-F—C₆H₄ | N | — |
| 102 | 2,4-Cl₂—C₆H₃ | C₂H₅ | 2-Cl—C₆H₄ | N | — |
| 103 | 2,4-Cl₂—C₆H₃ | benzyl | 2-Cl—C₆H₄ | N | — |
| 104 | 2,4-Cl₂—C₆H₃ | CH₃ | 4-Cl—C₆H₄ | N | — |
| 105 | 2,4-Cl₂—C₆H₃ | benzyl | 4-Cl—C₆H₄ | N | — |
| 106 | cyclohexyl | C₂H₅ | 4-F—C₆H₄ | N | — |
| 107 | cyclohexyl | benzyl | 4-F—C₆H₄ | N | — |
| 108 | cyclohexyl | C₂H₅ | 2-Cl—C₆H₄ | N | — |
| 109 | cyclohexyl | benzyl | 2-Cl—C₆H₄ | N | — |
| 110 | cyclohexyl | CH₃ | 4-Cl—C₆H₄ | N | — |
| 111 | cyclohexyl | benzyl | 4-Cl—C₆H₄ | N | — |
| 112 | tetrahydropyran-4-yl | CH₃ | 4-F—C₆H₄ | N | — |

TABLE-continued $$\overset{X}{\underset{N}{\diagup}}N-CH-\underset{R^1}{\overset{O}{C}}-CH-CH\overset{R^2}{\underset{R^3}{\diagdown}}$$

| Ex. | R¹ | R² | R³ | X | M.p./IR |
|---|---|---|---|---|---|
| 113 | 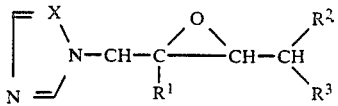 | benzyl | 4-F—C₆H₄ | N | — |
| 114 | 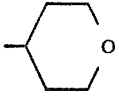 | CH₃ | 2-Cl—C₆H₄ | N | — |
| 115 | 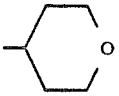 | benzyl | 2-Cl—C₆H₄ | N | — |
| 116 | 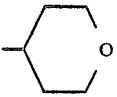 | CH₃ | 4-Cl—C₆H₄ | N | — |
| 117 | 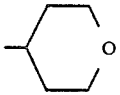 | benzyl | 4-Cl—C₆H₄ | N | — |
| 118 | tert.-butyl | CH₃ | 4-F—C₆H₄ | N | — |
| 119 | tert.-butyl | benzyl | 4-F—C₆H₄ | N | — |
| 120 | tert.-butyl | CH₃ | 2-Cl—C₆H₄ | N | — |
| 121 | tert.-butyl | benzyl | 2-Cl—C₆H₄ | N | — |
| 122 | tert.-butyl | CH₃ | 4-Cl—C₆H₄ | N | — |
| 123 | tert.-butyl | benzyl | 4-Cl—C₆H₄ | N | — |
| 124 | CH₃ | CH₃ | 4-F—C₆H₄ | N | — |
| 125 | CH₃ | benzyl | 4-F—C₆H₄ | N | — |
| 126 | 4-F—C₆H₄ | C₂H₅ | 4-F—C₆H₄ | CH | — |
| 127 | 4-F—C₆H₄ | CH₃ | 4-F—C₆H₄ | CH | — |
| 128 | 4-F—C₆H₄ | C₃H₇ | 4-F—C₆H₄ | CH | — |
| 129 | 4-F—C₆H₄ | C₄H₉ | 4-F—C₆H₄ | CH | — |
| 130 | 4-F—C₆H₄ | 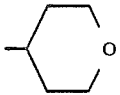 | 4-F—C₆H₄ | CH | — |
| 131 | 4-F—C₆H₄ | C₂H₅ | 2-F—C₆H₄ | CH | — |
| 132 | 4-F—C₆H₄ | iso-C₃H₇ | 4-F—C₆H₄ | CH | — |
| 133 | 4-F—C₆H₄ | 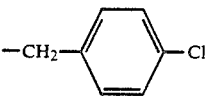 | 4-F—C₆H₄ | CH | — |
| 134 | 4-F—C₆H₄ | C₂H₅ | 2-Cl—C₆H₄ | CH | — |
| 135 | 4-F—C₆H₄ | 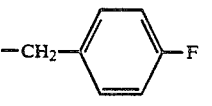 | 2-Cl—C₆H₄ | CH | — |
| 136 | 4-F—C₆H₄ | CH₃ | 3-Cl—C₆H₄ | CH | — |
| 137 | 4-F—C₆H₄ | 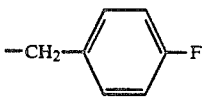 | 3-Cl—C₆H₄ | CH | — |
| 138 | 4-F—C₆H₄ | C₂H₅ | 4-Cl—C₆H₄ | CH | — |

TABLE-continued $$\left[\begin{array}{c} X \\ N-CH-C \\ N= \end{array} \begin{array}{c} O \\ \diagdown \\ R^1 \end{array} \begin{array}{c} R^2 \\ CH-CH \\ R^3 \end{array}\right]$$

| Ex. | $R^1$ | $R^2$ | $R^3$ | X | M.p./IR |
|---|---|---|---|---|---|
| 139 | 4-F—$C_6H_4$ | —$CH_2$—$C_6H_4$—Cl | 4-Cl—$C_6H_4$ | CH | — |
| 140 | 4-F—$C_6H_4$ | $C_2H_5$ | 2,4-$Cl_2$—$C_6H_3$ | CH | — |
| 141 | 4-F—$C_6H_4$ | $C_2H_5$ | 4-Br—$C_6H_4$ | CH | — |
| 142 | 4-Cl—$C_6H_4$ | $C_2H_5$ | 4-F—$C_6H_4$ | CH | — |
| 143 | 4-Cl—$C_6H_4$ | $C_2H_5$ | 3-Cl—$C_6H_4$ | CH | — |
| 144 | 4-Cl—$C_6H_4$ | $CH_3$ | 2,4-$Cl_2$—$C_6H_3$ | CH | — |
| 145 | 2-Cl—$C_6H_4$ | $C_2H_5$ | 2-Cl—$C_6H_4$ | CH | — |
| 146 | cyclohexyl | benzyl | 4-F—$C_6H_4$ | CH | — |
| 147 | cyclohexyl | $C_2H_5$ | 2-Cl—$C_6H_4$ | CH | — |
| 148 | 4-F—$C_6H_4$ | $C_7H_{15}$ | 2-Cl—$C_6H_4$ | N | 2954, 2928, 1507, 1273, 1140, 755 $cm^{-1}$ |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 34 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol, α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2′-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, cis-2-(1,2,4-triazolylmethyl)-2-(tert-butyl)-3(4-chlorophenyl)-oxirane (A) disclosed in DE 3 218 130.2 was employed.

USE EXAMPLE 1

Action on Wheat Brown Rust

Leaves of pot-grown wheat seedlings of the "Frühgold" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredient 1 has, when applied as a 0.025 wt % spray liquor, a better fungicidal action (97%) than prior art comparative agent A (60%).

USE EXAMPLE 2

Action on *Botrytis cinerea* in Paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results show that active ingredient 1, when applied as a 0.05% spray liquor, has a better fungicidal action (90%) than prior art comparative agent A (60%).

USE EXAMPLE 3

Action on *Pyrenophora teres*

Leaves of pot-grown barley seedlings of the "Igri" variety were sprayed to runoff at the 2-leaf stage with aqueous suspensions containing (dry basis) 80% of active ingredient and 20% of emulsifier. After 24 hours the plants were inoculated with a spore suspension of Pyrenophora teres and set up for 48 hours in a high-humidity climatic cabinet at 18° C. The plants were then cultivated for a further 5 days in the greenhouse at 20° to 22° C. and a relative humidity of 70%. The extent of the spread of the symptoms was then assessed.

The results show that active ingredient 1 has a good fungicidal action (97%) when applied as a 0.05% spray liquor.

We claim:

1. Azolylmethyloxirane of the formula I

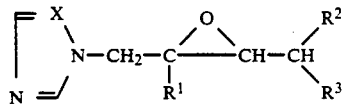

where
$R^1$ and $R^2$ are $C_1$–$C_{12}$-alkyl, benzyl, naphthyl, biphenyl, dioxanyl, phenyl, tetrahydropyranyl, tetrahydrofuranyl, norbornyl, $C_3$–$C_{12}$-cycloalkyl or $C_3$–$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms,
$R^3$ is $C_7$–$C_{12}$-alkyl, benzyl, naphthyl, biphenyl, dioxanyl, phenyl, tetrahydropyranyl, tetrahydrofuranyl, norbornyl $C_3$–$C_{12}$-cycloalkyl or $C_3$–$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms, and
X is N, or
plant-tolerated acid addition salts or metal complexes thereof.

2. An azolylmethyloxirane as set forth in claim 1, where $R^1$ is phenyl, $C_1$–$C_4$-alkyl or tetrahydropyranyl, $R^2$ is benzyl or $C_1$–$C_4$-alkyl, $R^3$ is phenyl, each of these radicals being unsubstituted or substituted by halogen, nitro, phenoxy, alkyl, alkoxy, amino or haloalkyl, where alkyl is of 1 to 4 carbon atoms.

3. A fungicidal composition comprising:
a carrier; and
an azolylmethyloxirane of the formula I

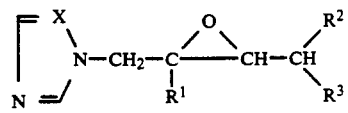

where $R^1$ and $R^2$ are $C_1$-$C_{12}$-alkyl, benzyl, naphthyl, biphenyl, dioxanyl, phenyl, tetrahydropyranyl, tetrahydrofuranyl, norbornyl, $C_3$-$C_{12}$-cycloalkyl or $C_3$-$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms, $R^3$ is $C_7$-$C_{12}$-alkyl, benzyl, naphthyl, biphenyl, dioxanyl, phenyl, tetrahydropyranyl, tetrahydrofuranyl, norbornyl $C_3$-$C_{12}$-cycloalkyl or $C_3$-$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms, and X is N, or a plant-tolerated acid addition salt or metal complex thereof, in a fungicidally effective amount.

4. A process for combating fungi, wherein a fungicidally effective amount of an azolylmethyloxirane of the formula I

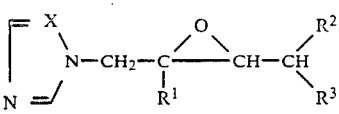

where $R^1$ and $R^2$ are $C_1$-$C_{12}$-alkyl, benzyl, naphthyl, biphenyl, dioxanyl, phenyl, tetrahydropyranyl, tetrahydrofuranyl, norbornyl, $C_3$-$C_{12}$-cycloalkyl or $C_3$-$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms, $R^3$ is $C_7$-$C_{12}$-alkyl, benzyl, naphthyl, biphenyl, dioxanyl, phenyl, tetrahydropyranyl, tetrahydrofuranyl, norbornyl $C_3$-$C_{12}$-cycloalkyl or $C_3$-$C_{12}$-cycloalkenyl, each of these radicals being unsubstituted or substituted by halogen, nitro, phenoxy, alkyl, alkoxy, amino or haloalkyl, where alkyl is of 1 to 4 carbon atoms, and X is N, or plant-tolerated acid addition salt or metal complex thereof, is allowed to act on the fungi, or plant materials, areas, plants or seed threatened by fungus attack.

5. A compound as set forth in claim 1, where $R^1$ is 4-fluorophenyl, $R^2$ is ethyl and $R^3$ is 4-fluorophenyl.

* * * * *